United States Patent [19]

Jansen et al.

[11] Patent Number: 5,788,989
[45] Date of Patent: Aug. 4, 1998

[54] DENDRIMER AND AN ACTIVE SUBSTANCE OCCLUDED IN THE DENDRIMER, A PROCESS FOR THE PREPARATION THEREOF AND A PROCESS FOR RELEASING THE ACTIVE SUBSTANCE

[75] Inventors: Johan F. G. A. Jansen, Eindhoven; Egbert W. Meijer, Waalre; Ellen M. M. De Brabander-Van Den Berg, Schinnen, all of Netherlands

[73] Assignee: DSM N.V., Netherlands

[21] Appl. No.: 454,026

[22] Filed: May 30, 1995

[30] Foreign Application Priority Data

May 27, 1994 [NL] Netherlands ............................ 9400880
Nov. 11, 1994 [NL] Netherlands ............................ 9401886

[51] Int. Cl.$^6$ ............................ A61K 9/14; A61K 47/48
[52] U.S. Cl. .............. 424/486; 424/78.17; 424/DIG. 16
[58] Field of Search ............................ 424/486, 78.17, 424/DIG. 16

[56] References Cited

U.S. PATENT DOCUMENTS

| | | | |
|---|---|---|---|
| 4,694,064 | 9/1987 | Tomalia et al. | 528/332 |
| 5,338,532 | 8/1994 | Tomalia et al. | 424/78.17 |
| 5,527,524 | 6/1996 | Tomalia et al. | 424/486 |
| 5,530,092 | 6/1996 | Meijer et al. | 528/363 |

FOREIGN PATENT DOCUMENTS

| | | |
|---|---|---|
| 271 180 B1 | 5/1993 | European Pat. Off. . |
| WO 88/01180 | 2/1988 | WIPO . |

OTHER PUBLICATIONS

M. Maciejewski, Concepts of Trapping Topologically by Shell Molecules, J. Macromol. Sci.–Chem., A17(4), pp. 689–703, 1982.

Tomalia et al., Angewandte Chemie. International Edition, dee129, nr.2, Feb. 1990, Weinheim De bladzijden 138–175, 'Starburst Dendrimers: Molecular–Level Control of Size, Shape, Surface Chemistry, Topology, and Flexibility from Atoms to Macroscopic Matter'.

Journal of Macromolecular Science–Chemistry, dee1A17, nr.4, 1982, bladzijden 689–703, 'Concepts of Trapping Topologically by Shell Molecules'.

Naylor et al., Journal of the American Chemical Society, dee1111, 1989, Washington, DC US, bladzijden 2339–2341, 'Starburst Dendrimers. 5. Molecular Shape Control'.

Angewandte Chemie, International Edition, dee130, nr.9, 1991, Weinheim De, bladzijden 1178–1180, 'Unimolecular Micelles', Newkome et al.

Journal of the Chemical Society, Perkin Transactions 1, nr.1, 7 Jan. 1994, Letchworth, GB, bladzijden 75–81, 'Synthesis, Metal–Binding Properties and Polypeptide Solubilization of "Crowned" Arborols', Nagasaki et al.

Primary Examiner—Joseph L. Schofer
Assistant Examiner—Wu C. Cheng
Attorney, Agent, or Firm—Cushman Darby & Cushman IP Group of Pillsbury Madison & Sutro, LLP

[57] ABSTRACT

The invention relates to a dendrimer composition in which an effective number of the terminal functionalities are provided with blocking agents, and at least one active substance species is occluded in the dendrimer. A blocking agent is a sufficiently sterically sized compound which readily enters into a chemical bond with a terminal group of a dendrimer but which can also be split off from the dendrimer or can be modified without affecting the chemical structure of the dendrimer and the occluded active substance. The blocking agent can also be provided with a protecting group. The time and duration over which an active substance is released can be controlled. The invention also relates to a process for the preparation of such a composition and to a process for the controlled release of the active substance.

16 Claims, No Drawings

DENDRIMER AND AN ACTIVE SUBSTANCE OCCLUDED IN THE DENDRIMER, A PROCESS FOR THE PREPARATION THEREOF AND A PROCESS FOR RELEASING THE ACTIVE SUBSTANCE

FIELD OF THE INVENTION

The present invention relates to a dendrimer composition comprised of a dendrimer and an active substance occluded in the dendrimer, a process for its preparation, and a process for releasing the occluded active substance from the dendrimer.

BACKGROUND OF THE INVENTION

Dendrimers are three-dimensional, highly branched oligomers and polymer molecules having a well defined chemical structure. Dendrimers in general comprise a core, a number of generations of ramifications (oftentimes called "branches") and an external surface. The generations of ramifications are composed of repeating structural units which radially extend outwardly from the dendrimer core. The external surface of a dendrimer of an Nth generation is, in general, composed of the terminal functional groups of the Nth (final) generation.

The empty volumes between the ramifications are essentially cavities. The shape and the dimensions of a cavity (sometimes referred to as a void) varies depending on the generation of the dendrimer and the chemical composition and structure of the repeating structural units within a generation or between generations. The shape and dimension of the cavities can be at least partially influenced during the preparation of the dendrimer such as by varying the repeating structural units, by increasing or decreasing the degree of branching, or by introducing discontinuities into the branches.

Dendrimers have reportedly functioned as carriers for agricultural, pharmaceutical and other materials, as is described in EP-B-271180 and U.S. Pat. No. 5,338,532, the complete disclosures of which are incorporated herein by reference. These carried materials may be associated with the dendrimers by various means. For instance, the carried material can be contained in the cavities of the dendrimer. Dendrimers of a higer generation have a large number of terminal groups which are spatially so close together that they form a molecular barrier, so that release of a carried material is diffusion controlled.

These heretofore known compositions suffer from a number of drawbacks. For instance, the carried materials are insufficiently close to the external surface of the dendrimer, and consequently, the time at which the release of the carried material starts cannot be controlled. There is therefore virtually continuous uncontrolled diffusion of the carried material from the dendrimer. In addition, the carried material in these compositions is not necessarily within the internal structure of the dendrimer, but may only be present on the surface of the dendrimer.

In principle, it is possible to occlude one or more guest molecules in a dendrimer if the preparation of the dendrimer is effected in the presence of guest molecules as described in M. Maciejewski, *I. Macromol. Sci. Chem.* A17 (4), pp. 689–703 (1982). At a specific generation, the density of terminal groups, is sufficiently large (congested) at the dendrimer surface that the outer shell is effectively blocked and is no longer permeable to guest molecules. The guest molecules may be divided statistically over the dendrimer or be concentrated in specific parts of the dendrimer. A drawback of the aforementioned process, however, is that guest molecules are occluded irreversibly in the dendrimer. In order to release the guest molecules, it is necessary to remove one or more generations of the dendrimer, which entails the disintegration of the entire dendrimer structure.

SUMMARY AND OBJECTS OF THE INVENTION

A dendrimer composition according to the present invention overcomes the drawbacks noted hereinabove.

The present invention includes at least one active substance which is occluded in the dendrimer, while permitting regulation over the initiation of its release from the dendrimer composition, as well as the relative duration during which active substances are released.

The composition according to the invention offers the further advantage that undesired compounds which are not occluded in the dendrimer, but are present, for instance, on the surface of the dendrimer, can readily be removed, for instance, by washing or dialysis. Based on the relaxation time measurements by means of NMR spectroscopy, it is presently considered that a surface layer consisting of blocking agents has solid state properties.

Surprisingly, it has also been disclosed that sometimes the active substance is stabilized through occlusion within the dendrimer. For example, it appears that colouring agents exhibit a higher resistance to light after occlusion in a dendrimer. The life of radicals appears to be considerably prolonged after occlusion in a dendrimer, e.g. the radical remains unreacted.

These and other objects are accomplished according to the present invention by blocking the terminal groups, or at least a sufficient number thereof, of the last generation of the dendrimer product whereby at least one active substance is effectively occluded within the dendrimer.

DETAILED DESCRIPTION OF THE INVENTION

A composition according to the present invention includes at least one dendrimer having an active substance at least partly occluded therein, wherein at least a sufficient number of the terminal groups on the final generation of the dendrimer are blocked with blocking agents. A blocking agent denotes a compound of sufficient steric size which readily enters into a bond, such as a chemical bond, with a terminal group of the dendrimer, but which can also be chemically or thermally, and readily split off from the terminal functional group of the dendrimer or can be modified without affecting the chemical structure, e.g. molecular architecture, of the dendrimer and the active substance occluded therein.

The blocking agent can be bound to the dendrimer in various manners, such as covalently, by hydrogen bonding, or by ionic bonding.

An active substance can be occluded completely or partly in the internal molecular structure of the dendritic macromolecule. Partly occluded active substances have a molecular portion extending outwardly from the dendritic macromolecule and at least another portion occluded within the dendrimer.

Blocking agents include compounds which can be split off from the dendrimer or can be modified, such as, for instance, by means of a chemical reaction.

Blocking agents include, among others, branched or non-branched Michael acceptors, active esters which also contain an ether and/or thiol group, optically active or optically inactive amino acids, nucleic acids, saccharides, isocyanates, aziridines, acid chlorides, anhydrides, aldehydes, ketones, acrylates, chiral epoxides, bislactides, fatty acids with an alkyl chain containing 12–24 carbon atoms and polymers. Additional Michael acceptors include isothyocyanates, sulphonylchlorides, phosphonyl chlorides. Representative Michael acceptors include polyethyleneglycol-4-nonyl-phenylether acrylate, polyethyleneglycol-phenylether acrylate, polyethylene glycol-phenylether methacrylate. Polymers include α-olefin polymers, such as polyethene and polypropene and nylons, such as nylon 4,6 and nylon 6. A particularly useful class of blocking agents are the amino acids, of which glycine, alanine, valine, leucine, isoleucine, phenylalanine, tyrosine, tryptophane, senine, threonine, methionine, cystine, proline, hydroxyproline, aspartic acid, glutamic acid, lysine, arginine and histidine are exemplary. Additonal examples include L-phenylalanine, L-glycine, L-alanine, and L-leucine.

The blocking agents can, if desired, be provided with one or more protective groups which can be the same or different. These protective groups can readily split off from the blocking agent without breaking the chemical bond between the blocking agent and the dendrimer, and without affecting the chemical structure of the dendrimer or the active substance. The blocking agents can be partly or completely protected with one or more protective groups.

Protective groups are described, for instance, in T. W. Green, *Protective Groups in Organic Synthesis*, (John Wiley & Son 1981). Chapter 7 of the aforesaid 1981 edition describes protection for the amino group, and is expressly incorporated herein by reference. The 1991 edition of said text also includes a chapter titled "Protection for the Amino Group", and that complete disclosure is incorporated herein by reference. Among the various described protective groups are, for instance, hydrolyzable esters, ethers, thiol groups, sulphonic acid groups, trityl, silyl, t-butoxy carbonyl ("BOC"), 9-fluorenyl methoxy carbonyl ("FMOC"), triphenyl methyl ("trityl"), benzyloxycarbonyl ("Z"), trimethyl silyl ethoxycarbonyl ("TEOC"), 2,7-di-t-butyl-[9-(10,10-dioxo-10,10,10,10-tetrahydrothioxanthyl)] methylcarbamate ("DBD-TMOC") 1,1,4,4-tetra-methyldisilyl azacyclopentene ("STABASE"), adamantyloxycarbonyl ("ADOC" or "AdMOC") and benzoSTABASE groups. Additional representative protective groups include benzyl, and t-butyl. The t-butoxy carbonyl group is a particularly effective protective group for purposes of the present invention.

The protective groups can be modified or split off from the blocking agent such as, for instance, by means of a chemical reaction, hydrolysis in a neutral, acidic or basic medium, a hydrogenation reaction, a thermal reaction, a photochemical reaction, a reaction in the presence of fluoride (such as, by analogy, breaking Si-Si or Si-O bonds in the presence of HF), or, for instance, by retro Michael condensation. Modification includes effecting physical modifications such as changing the molecular volume of the dendrimer, as well as conformational changes through the influence of, for example, temperature or solvent. For instance, by protonating all or a portion of the amine groups of a polypropylamine dendrimer, the repulsion between the dendrimer branches is increased, and an occluded active substance can be completely or partly released. These and other physical modifications can be applied to effect release of all or a portion the at least one active substance which is occluded or partially occluded.

According to the present invention blocking agents provided with protective groups include, for instance, methyloxyfuranone, aziridines provided with a sulphonic acid or t-butoxy carbonyl group, acrylates provided with large ester groups and amino acids provided with t-butoxy carbonyl, "FMOC," or Z groups.

A useful class of protected blocking groups are amino acids protected with one or more protecting (but "leavable") groups, such as BOC, FMOC or Z groups. For instance, representative amino acids protected with t-butoxy groups include, among others, t-butoxy carbonyl terminated L-phenylalanine, t-butoxy carbonyl terminated valine, and t-butoxy carbonyl terminated alanine.

In general, a particular blocking agent, protective group or blocking agent provided with a protective group, is selected based on the nature and generation of the dendrimer, and the molecular size of the occludable active substance.

In general, the number of terminal groups of the dendrimer that is provided with a blocking agent varies as a function of the nature and generation of the dendrimer applied and the nature and dimensions of the blocking agent. In practice the number of terminal groups provided with blocking agents is preferably such that the external surface is regarded as essentially closed and diffusion of the active substance out of the dendrimer is not possible. In general, at least about 30% of the terminal groups or functional groups on or at the external surface of the dendrimer are provided with a blocking agent. More particularly, at least about 50% of the terminal groups, or terminal functional groups, are blocked with a blocking agent. Still further, at least about 70% of such terminal groups are blocked with a blocking agent, and most particularly at least 90% are blocked.

In principle, all dendrimers can be used in the invention, including those described in *Angew. Chem. Int. Ed. Engl,.* 29: 138–175 (1990). Polyamidoamine (PAMAM) dendrimers, the core of which is an amine or ammonia and the ramifications of which are composed of, for instance, repeating

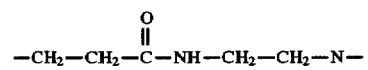

units are described therein.

By preference, the present dendrimer compositions contain at least one of the dendrimers described in PCT International WO-A-93-14147 and/or WO-A-9502008, the complete disclosures of which are incorporated herein by reference. The described polypropylamine (POPAM) dendrimers in PCT International WO-A-93-14147 and WO-A-9502008 have a core of 1,4-diaminobutane. The ramifications can, for instance, be formed from successive, repeating-$CH_2$-$CH_2$-$CH_2$-N units. Advantageously, these dendrimers possess high thermal stability, are soluble in diverse organic solvents, possess good stability in relation to hydrolysis, and contain accessible internal cavities and channels in which active substances can be occluded. Polypropylamine dendrimers can be easily be prepared on a commercial scale and are obtainable at high generations. The present compositions can, of course, be prepared using still other dendrimers.

Other dendrimer techniques are described in F. Vögtle et al., *Synthesis,* pp. 155–158 (Feb. 1978), the complete disclosure of which is incorporated herein.

According to the present invention, dendrimers having ramifications prepared from halogen cyanide units, such as units comprised of a monohalogenated hydrocarbon compound having 3 to 50 carbon atoms and at least 1 cyanide group, wherein the halogen and the cyanide group are separated from each other by at least 3 carbon atoms, can also be used. The carbon atom of the cyanide group does not form part of the 3–50 C-atoms of the hydrocarbon compound. The hydrocarbon compound is a saturated or unsaturated, linear or cyclic aliphatic group comprising at least three C-atoms. The hydrocarbon compound preferably has 3–15 C-atoms, and more preferably 3–7 C-atoms. The hydrocarbon compound may be branched or not. The hydrocarbon compound can contain one or more substituents which are inert with respect to a nucleophilic substitution reaction. In principle, such substituents can include, for example, amide, ester and nitro groups. The halogen cyanide unit preferably contains chlorine or bromine as halogen. Exemplary monohalogen by hydrocarbon compounds include, among others, aliphatic chlorocyanides such as mono-, di- and polycyanides of n-propyl chloride, n-butyl chloride, isobutyl chloride, pentyl chloride, isopentyl chloride, neopentyl chloride, hexyl chloride, heptyl chloride, actyl chloride, nonyl chloride, decyl chloride. Aliphatic bromocyanides include, among others, mono-, di- and polycyanides of n-propyl bromide, isobutyl bromide, n-butyl bromide, pentyl bromide, isopentyl bromide, neopentyl bromide, hexyl bromide, heptyl bromide, octyl bromide, nonyl bromide, decyl bromide. Cycloaliphatic cyanides include, among others, chloromethylene-cyclohexyl cyanide, bromomethylenecyclohexyl cyanide, chloromethylenecyclopentyl cyanide, bromomethylene-cyclopentyl cyanide. By preference, a halogen cyanide unit contains 1–20 cyanide groups, although more preferred are, respectively, halogen cyanide groups having 1–5 or 1–3 cyanide groups; and the halogen preferably is chlorine or bromine.

These dendrimers can be prepared starting from a core molecule having at least one functional group acting as nucleophile reactant in a nucleophilic substitution on a halogen cyanide. By preference, the functional group is a primary or secondary amine group. In a step (a) the preparation of such dendrimers the functional groups of the core molecule are reacted with at least one halogen cyanide unit. Next, in (b) each incorporated cyanide group is reduced to an amine, whereafter in a step (c) substantially each amine group is reacted with halogen cyanide units. The latter two reaction steps are repeated sequentially, but reiteratively, until the dendrimer of the desired generation is obtained. The process can be stopped after a step (b) or after a step (c).

Dendrimers according to the present invention can also be wholly or partly modified with various functional groups. This may be effected, for instance, by causing the available terminal groups to react, wholly or partly, optionally in the presence of a catalyst, with suitable reactants, of which some are described, for instance, in published PCT International Applications WO-A-9314147 and WO-A-9502008. A representative, but not restrictive, line of reagents includes, among others α,β-unsaturated compounds substituted with electron-withdrawing groups, unsaturated aliphatic esters and amides, such as, for instance, acrylic ester, methacrylic ester, crotylic ester and acrylamide, polyamides such as, for instance, nylon 4,6, nylon 6, nylon 6,10, nylon 8; epoxides such as ethylene oxide and propylene oxides; acid halides, such as for instance, acid chlorides, acryloyl chloride; alkyl halides, such as, for instance, epichlorohydrine, ethyl bromoacetate and allyl bromide; aryl halides, such as, for instance, benzyl chloride; tosyl halides, such as, for instance, tosyl chloride; anhydrides, such as, for instance, phthalic anhydride; dicarboxylic acids, such as, for instance, terephthalic acid and edipic acid; diols; (a)cyclic aldehydes such as formaldehyde, acetaldehyde, hexanal, benzaldehyde, pyridine aldehydes, p-formyl phenyl acetic acid and 1,4,5,8-naphthalene tetraacetaldehyde; ketones, such as for instance derivatized cyclohexanones (e.g. HALS compounds); lactide; lactones, such as for instance, caprolactone; phosphate esters as described U.S. Pat. No. 3,855,964; or molecules having a chiral centre. The dendrimer can be modified before the blocking agent is employed.

Dendrimers according to the invention are preferably symmetrically branched dendrimers. In general, dendrimers of the third or higher, more particularly the fourth or higher, and most particularly the fifth or higher generations are used.

According to the present invention, one or more molecules of one or more active substances are occluded in a dendritic macromolecule. The compositions of the present invention can therefore consist of a dendrimer having occluded therein an active substance from various classes such as pharmaceutical compounds, drugs, agrochemichals (such as pesticides, herbicides, insecticides, fungants, phenonones and toxins), materials in personal care products, cosmetics, food additives, additives for engineering plastics, chelating compounds, organic acids, non-metallic salts, radicals, soaps, signal generators (such as fluorescent or phosphorescent compounds), signal absorbers (such as UV absrobing compounds), dyes or colourants, metals, metal compounds, radionuclides, radioactive labelled compounds, D-II-A compounds, electron deficient and non-metallic electron rich compounds, and precursors of the above-mentioned compounds.

Representative pharmaceutically active compounds include, among others, steroids such as precursors to vitamins, bile acids; hormones; sterols such as mestranol, estradiol, estrogen, estrone; antibiotics, such as penicillin-V, azlocillin, and tetracyclines; neurotransmitters and immunochemicals such as monoclonal and polyclonal human IgA, IgG, or IgM and bovine IgG. Represenative precursors to pharmaceutically active compounds include benzoic acid, benzaldehyde, phenol, aliphatic and heterocyclic amines and derivatives thereof.

Representative agrochemicals include fertilizers, such as acid phosphates and sulfates; insecticides such as chlorinated hydrocarbons (such as p-dichlorobenzene), imidazoles, and pyrethrins, including natural pyrethrins; herbicides include carbamates, derivatives of phenol and derivatives of phenol and derivatives of urea; and pheromones such as the natural and synthetic pheromones, such as 4-methyl-3-heptanone.

Representative food additives include flavors, fragrances and intensive sweeteners such as, for instance, as aspartame, saccharine, acesulfam-K and sucralose.

Representative organic acids or non-metallic salts include monocarboxylic acides polycarboxylic acids such as saturated or unsaturated aliphatic acids, unsubstituted aromatic acids, substituted aromatic acids, and salts thereof. Representative saturated aliphatic monocarboxylic acids include formic acid, acetic acid, propionic acid, n-butyric acid, isobutyric acid, n-valeric acid, caproic acid. Representative substituted aliphatic acids include glycolic acid, lactic acid, acrylic acid. Representative polycarboxylic acids include oxalic acid, malonic acid, succinic acid, glutaric acid, adipic acid, tartaric acid, maleic acid, fumaric acid and salts thereof. Representative aromatic acids include benzoic acid, phthalic acid, salycilic acid, anthranilic acid, cinnamic acid. Representative organic acids also include 3,5-dinitrobenzoic acid, 3,5-dimethoxybenzoic acid, 4-cyanobenzoic acid and anilinonaphtalenesulphonic acid. Representative non-metallic salts include the ammonium salt of anilinonaphtalenesulphonic acid.

Representative radicals or "radical-formers" include hexamethylimidazolium-1-yloxy methylsulphate, diphenylpicrylhydrazyl, BPDA-complex ($\alpha$-$\tau$-bisdiphenylene-$\beta$-phenylallyl), 2,2,6,6,tetramethyl-1-pyperidinyloxy, doxyl (4,4-dimethyl-3-oxayolinyloxy-(4,4-dimethyloxayolidine-N-oxyl)), proxyl, proxylcarboxylic acid, and derivatives thereof.

Representative signal absorbers include non-linear optical compounds, such as p-nitrodimethylaniline and dimethylaminonitrostilbene; UV absorbing compounds such as azanaphtol compounds and crystalviolet; fluorescent compounds such as eosine B, rhodamide B, flourescine and derivatives thereof.

Representative soaps include sulphate soaps, phosphoric acid soaps, pyridine soaps, and alkaline fatty acid soaps. Representative phosphoric acid soaps include diphenylphosphonic acid and phenylphosphonic acid. Representative pyridine soaps include dodecylpyridiniumchloride. Alkaline soaps and heavy metal soaps include aluminum, cobalt, calcium, zinc and lead soaps.

Representative colourants include crystal violet, brilliant green, erichrome black T, methyl red, methyl orange, alizarin yellow, and Bengal pink, as well as merocyanine colourants.

Representative electron deficient compounds include compounds that are electron deficient in the excited state, and organic compounds provided with electron withdrawing groups conjugated or non-conjugated, such as carboxylic acid groups, amide groups, imide groups, cyano groups, sulphon groups, chinones, and hydrochinones. Organic cyano compounds include tricyanoethylene, tetracyanodihydroquinone and tetra cyanohydrochinon. Representative radionucleotides include isotopes, such as isotopes of uranium, iodine, and krypton.

Representative metals can be selected from among the metals in one or more of Groups 1 through 14 of the Periodic Table and the Lanthanides and Actinides (Handbook of Chemistry, 70th Edition (1989–90)). More particularly, exemplars of a metal from Group 1 are Na, K, Rb, and Cs; from Group 2 are Mg and Ca; from Group 6 are Cr and Mo; from Group 8 are Fe and Ru; from Group 9 are Co, Rh, and Ir; from Group 10 are Cu and Ag; from Group 12 is Zn; from Group 13 is Al; and from Group 14 are Sn and Pb. For instance, a dendritic catalyst carrier can comprise a blocked dendrimer having occluded therein catalytically active metal (s), which occluded metals can be released.

Representative metal compounds include inorganic as well as organic or organometallic compounds. Among the metal compounds are metal salts such as alkali metal sulfates, halides and carbonates, of which sodium sulfate, sodium chloride and sodium carbonates are illustrative. Other metal salts such as copper chloride or iron chloride can also be occluded within a blocked dendrimer.

In the composition according to the present invention, it is therefore preferred that the active substance is not chemically bonded to the dendrimer. It is preferred that the active substance according to the invention is in essence occluded physically within the dendrimer. This offers the advantage that the active substance is not chemically modified.

Depending on the molecular shape and the dimensions of an active substance, the person skilled in the art will select the most suitable generation of the dendrimer. For instance, in the case of POPAM dendrimers, dendrimers of generation 4 or higher can be utilized such as dendrimers of the 4th through 7th generations.

The quantity, e.g. number of molecules, of an active substance which can be occluded in a dendritic macromolecule depends on, among other things, the chemical composition and structure of the dendrimer, the shape and dimensions of the cavities in the dendrimer, the generation of the dendrimer and the shape and dimensions of the molecules of the active substance to be occluded.

A composition comprising a dendrimer provided with the blocking agents and an active substance occluded within the dendrimer can be readily prepared. An amount of the active substance to be occluded is added to a reaction mixture containing the dendrimer or dendrimers. An amount of the blocking agent to be applied can be added concurrently, with or simultaneously with the active substance. The amount of blocking agent can also, if desired, be added after the active substance has been added to the reaction mixture.

Advantageously, dendrimer compositions are obtained that can be washed or subjected to dialysis without loss of active substance. This process has the additional advantage that any undesired substances present can be washed away without loss of the occluded active substance occurring. By preference the blocking agent is added after the active substance.

Controlled release of the occluded active substance is also achievable by separating out, e.g. splitting off, or modifying the blocking agent. Modifying a blocking agent as described elsewhere herein, means modification of the physical interaction between a blocking agent and the dendrimer or between the blocking agents themselves, as a result of which the occluded active substance is released. This process offers the advantage that the structure of the dendrimer with blocking agents remains intact and can be re-used. In one embodiment, the active substance is released by splitting off the protective group. In another embodiment, an active substance is released by first splitting off the protective group and then splitting off the blocking agent. Such a process offers the further advantage that specific occluded active substances can be released in a controlled way. Staggered splitting (or modification), e.g., splitting off the protecting groups followed by splitting off the blocking group, permits controlled release of different molecular sized active substances from the dendrimer. Splitting off the protective group essentially enables release of smaller molecules of the active substance such as from within the dendrimer. Splitting off the blocking agent essentially enables release of larger-sized active substance molecules. Furthermore, control can be further exerted through judicious selection of the size of the blocking agent as well as the protective group whereby retarded release of an active substance can be ensured, such as by splitting off protective group, so that the dendrimer composition finds efficacious utility in applications calling for slow-release of at least one active substance. Representative slow release and/or controlled release compositions are described in Example LXXV and in Tables 3b and 3c.

Processes for splitting off and/or modifying the blocking agent according to the invention include, for instance, a chemical reaction, hydrolysis in a neutral, acidic or basic medium, a hydrogenation reaction, a thermal reaction (such as heating), a photochemical reaction, a reaction in the presence of fluoride, or a retro Michael condensation. The blocking agent is preferably removed by hydrolysis in an acidic medium. These processes are also suitable for splitting off a protective group or a blocking agent provided with one or more protective groups.

Dendrimers having active substances occluded therein, processes for their preparation, and processes for the controlled release of active substances are described in Netherlands Application No. 940080 filed on May 27, 1994, Netherlands Application No. 9401886 filed Nov. 11, 1994, and EPO Application 95201373.8, filed May 24, 1995, the complete disclosures of which are incorporated herein by reference.

The invention is further described in the following non-limiting Examples.

EXAMPLES

In these Examples, the NMR spectra were measured with a Bruker AM400 or a Varian Gemini 300 spectrometer in chloroform. ESR spectra were measured with a Bruker ER 200D SRC spectrometer, an X-ray band and a standard measurement cell. The temperature was measured with a Bruker ER 4111 thermometer. Low-temperature ESR spectra were measured in chloroform. Infrared spectra were measured with a Perkin Elmer 1600 FT-IR spectrometer. Specific rotations were determined with a JASCO DIP 370 polarimeter.

Example I

Occlusion of 3,5-dinitrobenzoic Acid

An amount of 3,5-dinitrobenzoic acid (200 mg) was added to a mixture of 35 mg (4.9 μmol) of a $NH_2$-terminated polypropylamine dendrimer of the fifth generation (64-cascade: 1,4-diaminobutane[4]:(1-azabutylidene)$^{60}$:propylamine) and 0.2 ml of triethylamine in 10 ml of dichloromethane. After stirring for 30 minutes, an amount of the hydroxysuccinimide ester of N-BOC-L-phenylalanine (114 mg 0.3 mmol) was added to the reaction mixture. After stirring for one night the reaction mixture was diluted to 50 ml with dichloromethane and next washed three times with water (30 ml per wash) and three times with saturated sodiumcarbonate solution (30 ml for each wash). After drying in the presence of sodiumsulphate and evaporation of the remaining liquid, $^1$H NMR analysis showed that 15–25 molecules of 3,5-dimethoxybenzoic acid were occluded in the dendrimer. 80% of the dendrimer was isolated.

Example II

Occlusion of 3,5-dimethoxybenzoic Acid

An amount 3,5-dimethoxybenzoic acid (200 mg) was added to a mixture of a $NH_2$-terminated polypropylamine dendrimer (22 mg; 3.1 μmol) of the fifth generation (64-cascade: 1,4-diaminobutane[4]:(1-azabutylidene)$^{60}$:propylamine) and 0.2 ml of triethylamine in 10 ml of dichloromethane to form a reaction mixture. After stirring for 30 minutes, the hydroxysuccinimide ester of N-BOC-L-phenylalanine (72 mg; 0.19 mmol) was added to the reaction mixture. After stirring for one night the reaction mixture was diluted to 50 ml with dichloromethane and next washed three times with water (30 ml per wash) and three times with a saturated sodiumcarbonate solution (30 ml per wash). After drying in the presence of sodiumsulphate and evaporation of the remaining liquid, $^1$H NMR analysis showed that 15–25 molecules of 3,5-dimethoxybenzoic acid were occluded in the dendrimer. About 85% of the dendrimer was isolated.

Example III

Occlusion and Release of Proxylcarboxylic Acid (radical)

An amount of proxylcarboxylic acid (8 mg) was added to a mixture of a $NH_2$-terminated polypropylamine dendrimer (59 mg) of the fifth generation (64-cascade: 1,4-diaminobutane[4]:(1-azabutylidene)$^{60}$:propylamine) and 0.4 ml of triethylamine in 10 ml of dichloromethane. After stirring for 30 minutes at room temperature, the hydroxysuccinimide ester of N-BOC-L-phenylalanine (191 mg; 0.53 mmol) was added. After stirring for one night the reaction mixture was diluted to 50 ml with dichloromethane and next washed three times with water (30 ml per wash) and three times with a saturated sodiumcarbonate solution (30 ml per wash). After drying in the presence of sodiumsulphate and evaporation of the remaining liquid, the yield was about 70%. ESR spectroscopy confirmed that a few proxylcarboxylic acid radicals were occluded in the dendrimer.

Next, the dendrimer containing proxyl radicals was washed 16 times with 50 ml of a saturated sodium carbonate solution. Since the intensity of the signal corresponding to the radical was unchanged after washing, it was assumed that the radical was occluded in the dendrimer. From comparison with the spectrum of the free radical it was concluded that about 1 radical per dendrimer molecule was occluded.

Next, the radical-containing dendrimer (34 mg) was dissolved in dichloromethane (5 ml), to which concentrated HCl (1 ml) was added. After stirring for about 60 hours, water (4 ml) was added. The acid water layer was extracted by means of 5 portions of dichloromethane (5 ml), dried over sodiumsulphate and boiled down, after which dichloromethane (5 ml) was added for measurement of the ESR spectrum. By means of ESR the presence of proxyl radicals in the dichloromethane solution was demonstrated.

After the radical-containing dichloromethane solution had been washed with a saturated sodiumcarbonate solution, no free proxyl radicals were detected in the dichloromethane layer. This implies that only the radicals released out of the dendrimer were extracted by means of sodiumcarbonate. It also means that sodiumcarbonate is not able to extract the radicals occluded in the dendrimer.

Example IV

Blank Experiment A

Example IV shows that the proxyl radical is not bonded chemically to the dendrimer.

An amount of proxylcarboxylic acid (10 mg) was added to a solution of dicloromethane (0.5 ml) and a $NH_2$-terminated polypropylamine dendrimer (5 mg) of the fifth generation (64-cascade: 1,4-diaminobutane[4]:(1-azabutylidene)$^{60}$:propylamine), provided with BOC-terminated L-phenylalanine. The mixture was stirred for 24 hours at room temperature, then diluted to 5 ml with dichloromethane, washed three times with water (10 ml per wash) and four times with a saturated sodiumcarbonate solution (10 ml per wash).

After drying the mixture over sodiumsulphate and boiling down, it was demonstrated with ESR that the dendrimer contained no proxyl radicals. This shows that the proxyl radical is not bonded chemically to the amino acid.

Example V

Blank Experiment B

An amount of proxylcarboxylic acid (proxyl radical) (21 mg; 0.12 mmol) was added to a mixture of 10 mg (13 μmol) of a N $H_2$-terminated polypropylamine dendrimer of the second generation (8-cascade: 1,4-diaminobutane[4]:(1- azabutylidene)⁴:propylamine) and 0.1 ml of triethylamine in 0.25 ml of dichloromethane. After stirring for 30 minutes at room temperature 37 mg (0.10 mmol) of the hydroxysuccinimide ester of N-BOC-L-phenylalanine was added to the reaction mixture. After stirring for one night at room temperature, the reaction mixture was diluted to 50 ml with dichloromethane and next washed three times with 30 ml of water and three times with 30 ml of a saturated sodiumcarbonate solution. After drying over sodiumsulphate and boiling down, the yield was about 81%.

The ESR spectrum of the dendrimer dissolved in dichloromethane showed a trace of the proxyl radical.

The radical was completely removed by washing five times with 30 ml of a saturated sodiumcarbonate solution.

This shows that the proxyl radical is not bonded chemically to the dendrimer.

Example VI

Occlusion of Several Proxylcarboxyl Radicals Per Dendrimer

An amount of proxylcarboxylic acid (58 mg; 0.31 mmol) was added to a mixture of a $NH_2$-terminated polypropylamine dendrimer of the fifth generation (64-cascade: 1,4-diaminobutane[4]:(1-azabutylidene)$^{60}$:propylamine) (22 mg; 3 μmol) and 0.1 ml of triethylamine in 0.5 ml of dichloromethane. After stirring for 30 minutes, 95 mg (0.26 mmol) of the hydroxysuccinimide ester of N-BOC-L-phenylalanine was added.

The procedure as described in Example III was repeated.

By means of ESR it was demonstrated that eight radicals per dendrimer molecule were occluded.

Example VII

Occlusion of Proxylcarboxylic Acid in BOC-protected Leucine

The procedure as described in Example III was repeated, using 0.53 mmol of the hydroxysuccinimide ester of BOC-protected leucine instead of the hydroxysuccinimide ester of BOC-phenylalanine. About 1 proxylcarboxylic acid radical per dendrimer molecule was occluded.

Examples VIII–XI

The procedure as described in Example I was repeated. In Table 1 a summary is presented of the quantities applied and the active substances used.

TABLE 1

| Active substance | quantity of dendrimer (mg) | quantity of amino acid (mg) | quantity of active substance (mg) | load |
|---|---|---|---|---|
| 8. Reichardt E$_T$ probe | 38 | 127 | 11 | 2 |
| 9. Kosover R-probe | 25 | 82 | 3.3 | 0.7 |
| 10. Penicillin V | 39 | 129 | 39 | 2 |
| 11. Azlocillin (penicillin) | 119 | 391 | 18 | 0.3 |

Reichardt E$_T$ probes are used for the determination of the polarity of a solvent using UV-spectroscopy.

Kosover refers to 2,6,-diphenyl-4-(2,4,6-triphenylpyridinio)phenolate.

Examples XII–LXVIII

In the following Examples XII–LXVIII diverse active substances were occluded in a dendrimer: radicals, colourants, merocyanine colourants, fluorescent compounds, chelating compounds, azanaphthol compounds (which become chiral through occlusion in the dendrimer), electron-poor compounds and pyridine soaps.

Standard Procedure for Loads up to 1.2 Molecules of Active Substance Per Dendrimer X mg of an active substance was added to a mixture of Y mg of a $NH_2$-terminated polypropylamine dendrimer of the fifth generation (64-cascade: 1,4-diaminobutane[4]:(1-azabutylidene)$^{60}$:propylamine) and 0.1 ml of triethylamine in 10 ml of dichloromethane. After stirring for 30 minutes, 1 equivalent of the hydroxysuccinimide ester of N-BOC-L-phenylalanine was added per $NH_2$ group present in the dendrimer. The reaction mixture was stirred overnight. Then the reaction mixture was diluted to 50 ml with dichloromethane and subsequently washed three times with 30 ml of water and three times with 30 ml of a saturated sodiumcarbonate solution. After drying over sodiumsulphate and evaporation of the remaining liquid, the dendrimer containing active substance was isolated.

Standard Procedure for Loads Higher than 1.2 Molecules of Active Substance Per Dendrimer In this case 0.5 ml of triethylamine and 0.5 ml of dichloromethane, respectively, were used instead of 0.1 ml of triethylamine and 10 ml of dichloromethane.

Table 2 summarizes the active substances used, the quantities of dendrimer, protected amino acid and active substance used and the quantity of active substance that was occluded per dendrimer molecule.

TABLE 2

| | quantity of | | | | |
|---|---|---|---|---|---|
| Active substance | dendrimer (mg) | amino acid (mg) | active substance (mg) | load* | yield (%) |
| 4-cyanobenzoic acid | 45 | 145 | 13 | 0.4 | 44 |
| | 76 | 246 | 146 | 5 | 26 |
| ANS acid | 58 | 188 | 9 | 3 | 60 |
| | 41 | 133 | 109 | 20 | 90 |
| ANS NH4 salt | 53 | 171 | 10 | 1 | 63 |
| | 78 | 252 | 100 | 10 | 79 |
| DPHT | 65 | 211 | 10 | 2 | 49 |
| | 97 | 308 | 95 | 20 | 76 |
| radicals | | | | | |
| hexamethylimidazolium,-1-yloxy methyl sulphate | 58 | 188 | 14 | 4 | 64 |
| diphenylpicrylhydrazal | 48 | 155 | 21 | 0.2 | 59 |
| BDPA complex | 48 | 156 | 8 | 0.2 | 72 |
| phosphoric acid soaps | | | | | |
| diphenylphosphonic acid | 23 | 74 | 23 | 0.5 | 57 |
| " | 33 | 107 | 117 | 1 | 50 |
| phenylphosphonic acid | 21 | 68 | 21 | 0.3 | 25 |
| " | 34 | 110 | 101 | 1 | 45 |
| pyridine soap | 51 | 165 | 110 | 1 | 82 |
| dodecylpyridinium-chloride | | | | | |
| colourants | | | | | |
| crystal violet | 20 | 64 | 17 | 1.2 | 75 |
| " | 79 | 225 | 260 | 8 | 55 |
| brilliant green | 32 | 103 | 14 | 1 | 65 |

TABLE 2-continued

| Active substance | dendrimer (mg) | amino acid (mg) | active substance (mg) | load[a] | yield (%) |
|---|---|---|---|---|---|
| eriochrome black T | 26 | 84 | 10 | 0.15 | 70 |
| methyl red | 22 | 71 | 15 | 0.1 | 80 |
| methyl orange | 30 | 97 | 10 | 0.1 | 62 |
| alizarin yellow | 26 | 84 | 10 | 0.1 | 62 |
| Bengal pink | 51 | 165 | 10 | 1 | 65 |
|  | 76 | 246 | 306 | 4 | 55 |
| merocyanine colourants |  |  |  |  |  |
| spironaphthalene[d] | 34 | 110 | 22 | 8 | 88 |
| cl-spironaphthalene[e] | 36 | 117 | 29 | 8 | 90 |
| NO$_2$-spironaphthalene[f] | 52 | 168 | 15 | 4 | 98 |
| spiroanthr[g] | 50 | 162 | 16 | 4 | 77 |
| cl-spiroanthr[h] | 86 | 278 | 40 | 3 | 75 |
| electron-deficient compounds |  |  |  |  |  |
| tricyanoethylene | 49 | 160 | 50 | b | 68 |
| tetracyanodihydro-quinone | 111 | 364 | 215 | b | 70 |
| steroid |  |  |  |  |  |
| mestranol | 125 | 405 | 39 | 2 | 64 |
| fluorescent compounds |  |  |  |  |  |
| eosin B | 30.5 | 98 | 23 | 1 | 97 |
|  | 47 | 151 | 197 | 2 | 58 |
| rhodamide B | 37 | 119 | 10 | 1 | 99 |
|  | 353 | 1143 | 800 | 4 | 79 |
| rhodamide B base | 28.6 | 93 | 23 | 4 | 95 |
| fluorescein | 35 | 113 | 14 | 0.5 | 79 |
|  | 193 | 623 | 1050 | 4 | 50 |
| fluorescein Na salt | 33 | 106 | 50 | 0.5 | 78 |
| fluorescein diacetate | 63 | 203 | 238 | 4 | 82 |
| dinitrofluorescein | 30 | 100 | 13 | b | 71 |
| chelating compounds |  |  |  |  |  |
| aluminon | 28 | 91 | 96 | 2 | 85 |
|  | 69 | 224 | 43 | 6 | 65 |
| aurin tricarboxylic acid | 56 | 181 | 314 | 2 | 75 |
|  | 32 | 104 | 20 | 10 | 81 |
| azanaphthol compounds |  |  |  |  |  |
| new coccin | 50 | 162 | 20 | 0.5 | 89 |
|  | 55 | 178 | 250 | 2 | 74 |
| blue hydroxynaphthol | 55 | 178 | 24 | 0.5 | 74 |
|  | 37 | 120 | 229 | 2 | 94 |
| crystal scarlet | 37 | 120 | 20 | 0.2 | 71 |
|  | 34 | 110 | 260 | 1.4 | 50 |
| Ph indicators |  |  |  |  |  |
| orange II | 56 | 181 | 20 | 0.1 | 66 |
| orange G | 34 | 110 | 18 | 0.4 | 88 |
| indigo carmine | 46 | 150 | 23 | c | 67 |

[a]in molecules of active substance per dendrimer molecule
[b]substance is occluded in the dendrimer. Owing to a too great shift of the UV absorption it is not possible to determine the load.
[c]substance is occluded in the dendrimer. Owing to the insolubility of the starting material it was not possible to determine the load.
[d]1,3-dihydro-1,3,3-trimethylspiro-{2H-indole-2,3'-[3H]naphth[2,1-b][1,4-oxazine]}
[e]5-chloro-1,3-dihydro-1,3,3-trimethylspiro-{2H-indole-2,3'-[3H]naphth[2,1-b][1,4-oxazine]}
[f]1',3'-dihydro-1',3',3'-trimethyl-6spironitro-[2H-benzopyrane-2-2'-(2H)indole]
[g]1,3-dihydro-1,3,3-trimethylspiro-{2H-indole-2,3'-[3H]phenanthr[9,10-b][1,4-oxazine]}
[h]5-chloro-1,3-dihydro-1,3,3-trimethylspiro-{2H-indole-2,3'-[3H]phenanthr[9,10-b][1,4-oxazine]}
ANS = anilinonaphthalene sulphonic acid
DPHT = diphenylhexatriene The UV spectra demonstrates that the colourants listed in Table 2 were occluded in the dendrimer. For instance, the UV spectrum signal of the N-containing colourants occluded in dendrimer shows a clear shift relative to the signal of the free colourant. Bengal pink shows no signal in the UV spectrum and no fluorescence. However, after occlusion of the Bengal pink in the dendrimer a clear fluorescence spectrum was observed.

Additionally, colourants, such as eriochrome black T and alizarin yellow, were actually occluded in the dendrimer. This was demonstrated by ready experiment. A sample flask was filled with eriochrome black T dissolved in acetonitrile, which resulted in a reddish brown solution. A second sample flask was filled with a mixture of acetonitrile and dendrimer containing eriochrome black. The dendrimer does not dissolve in acetonitrile. The acetonitrile solution remained colourless. The colourant was observed in the form of black spots on the glass surface. The solution remained colourless even after a 2-hour ultrasonic treatment and after standing untreated for 6 weeks'. The colourant was actually occluded in the dendrimer and was not released from the dendrimer having terminal groups blocked with phenylalanine in which the blocking agent protected with a BOC group.

Example LXIX

Blank Experiment C

Example LXIX demonstrates that the active substance is not bonded chemically to the amino acid.

A mixture of 200 mg of the hydroxysuccinimide ester of N-BOC-L-phenylalanine, 100 mg of alizarin yellow and 10 ml of dichloromethane was stirred for 4 days at room temperature. Next, 50 mg of an amine-terminated second-generation polypropylamine dendrimer (8-cascade: 1,4-diaminobutane[4]:(1-1-azabutylidene)$^4$:propylamine) was added to the mixture and the mixture was stirred for overnight at room temperature. The mixture was diluted to 50 ml with dichloromethane and then separately washed using 30 ml of a saturated sodiumcarbonate solution. After drying in the presence of sodiumsulphate and evaporation, the dendrimer was isolated. The yield was 63%. The quantity of occluded alizarin yellow was negligibly small: 0.001 molecules per dendrimer. This shows that the alizarin yellow is not bonded chemically to the amino acid.

Subsequently the dendrimer was dissolved in dichloromethane and again washed four times with each wash using 30 ml of a saturated sodiumcarbonate solution. After drying the solution over sodiumsulphate and boiling down, there was no remaining occluded alizarin yellow based on the determination of an average of 0.0001 molecules per dendrimer molecule.

Example LXX-LXXI

Occlusion of Metal Salts 50 mg of CuCl$_2$ and FeCl$_3$, respectively, was added to 86 mg of a NH$_2$-terminated polypropylamine dendrimer of the fifth generation(64-cascade: 1,4-diaminobutane [4]:(1-azabutylidene)$^{60}$:propylamine) and 0.1 ml of triethylamine in 10 ml of dichloromethane. After stirring for 30 minutes 310 mg of the hydroxysuccinimide ester of N-BOC-L-phenylalanine was added. The reaction mixture was stirred overnight. Next, the reaction mixture was diluted to 150 ml with dichloromethane and successively washed six times with 100 ml of a saturated sodiumcarbonate solution. After drying over sodiumsulphate and evaporation of the remaining liquid, the dendrimer containing active substance was isolated. In both cases, two molecules of salt were loaded (occluded) per dendrimer.

Example LXXII

Example I was repeated in the presence of 38 mg of a polypropylamine dendrimer of the sixth generation (128-Cascade: 1,4-diaminobutane[4]:1-azabutylidene)$^{124}$:propylamine), 100 mg of the hydroxysuccinimidic ester of t-BOC-alanine and 227 mg of dinitrobenzoic acid. Approximately 8 molecules of nitrobenzoic acid were occluded in the dendrimer. Approximately 70% of the terminal amine groups of the dendrimer were modified with t-BOC-alanine.

Example LXXIII

Example I was repeated in the presence of 134 mg of a polypropylamine dendrimer of the fourth generation (32-Cascade:1,4-diaminobutane[4]:(1-azabutylidene)$^{28}$. propylamine), 490 mg of the hydroxylsuccinimidic ester of t-BOC-tryptophane and 286 mg of Bengale pink. Approximately 2 molecules of Bengale pink were occluded in the dendrimer. Approximately 71% of the terminal groups of the dendrimer were modified with t-BOC-tryptophane.

Example LXIV

Occlusion and Selective Release of Two Different Active Substances

Example I was repeated in the presence of 99 mg of a polypropylamine dendrimer of the fifth generation (64-Cascade:1,4-diaminobutane[4]:(1-azabutylidene)$^{60}$:propyll amine), 278 mg of the hydroxysuccinimidic ester of t-BOC-valine and 254 mg of dinitrobenzoid acid (active substance I) and 236 mg of Bengale pink (active substance II). Respectively 10 molecules of dinitronbenzoic acid and 4 molecules of Bengale pink were occluded in the dendrimer.

After refluxing for 2 hours in formic acid and dialysis for 2 days in chloroform, the load of Bengale pin was 4 molecules per dendrimer molecule. Dinitrobenzoic acid was completely removed from the dendrimer.

After refluxing for 2 hours in hydrochloric acid and overnight dialysis in water, the load of Bengale pink was 0.005 molecules per dendrimer molecule.

The dendrimer was recovered as a fifth generation amine terminated dendrimer.

All t-BOC-valine groups were removed from the dendrimer.

Example LXXV

Example I was repeated in the presence of 99 mg of a polypropylamine dendrimer of the fifth generation (64 Cascade:1,4-diaminobutane[4]:(1-azabutylidene)$^{60}$:propylamine), 278 mg of the hydroxysuccinimidic ester of t-BOC-valine and 75 mg of nitrophenol (active substance I) and 25 mg methylviolet 3 RAX (Aldrich) (active substance II) and a number of different blocking agents as shown in Table 3a.

TABLE 3a

| Blocking agent | mg pa | mg ester | Y (%) | Load (I) | Load (II) |
|---|---|---|---|---|---|
| N-FMOC-β-butyl-aspartic-hydroxysuccinimide ester* | 51 | 236 | 40 | 8 | 8.2 |
| N-FMOC-O-t-butyl-L-serine-3,4-dihydro-4-oxo-1,2,3-benztriazole | 48 | 227 | 82 | 4 | 3.9 |

TABLE 3a-continued

| Blocking agent | mg pa | mg ester | Y (%) | Load (I) | Load (II) |
|---|---|---|---|---|---|
| N-FMOC-L-phenyl-alanine-pentafluorophenylester | 90 | 447 | 52 | 8 | 7.6 |
| N-FMOC-S-trityl-L-cystoine pentafluorophenylester | 71 | 478 | 53 | 4 | 4.2 |
| N-FMOC-L alaninepentafluorophenyl-ester | 49 | 208 | 79 | 8 | 7.8 |

*After working up, 50% of the FMOC seemed to be lost.

Active substance I was selectively released by first stirring the conjugate with a 20% solution of piperidine in dimethylformamide followed by (6 times) dialysis in ethanol. The loads of respectively nitrophenol (I) and methylviolet 3 RAX (II) are shown in Table 3b.

TABLE 3b

| Blocking agent | Load (I) | Load (II) |
|---|---|---|
| N-FMOC-β-t-butyl-asparatic hydroxysuccinimide-ester | 0 | 3.9 |
| N-FMOC-O-t-butyl-L-serine-3,4-dihydro-4-oxo-1,2,3-benztriazole | 0 | 3.7 |
| N-FMOC-L-tenylalanine-pentafluorophenylester | 0 | 7.3 |
| N-FMOC-S-trityl-L-cysteine-pentafluorofonylester | 0 | 4.0 |
| N-FMOC-L-alanine-pentafluorophenylester | 0 | 0.05 |

The conjugate was then boiled for two hours in a solution of 6N hydrochloric acid. The solvent was evaporated and the remaining solution was neutralized. The conjugate was then subjected successively to a dialysis in ethanol and a dialysis in water. The loads of nitrophenol (I) and methylviolet 3 RAX (II) are shown in Table 3c.

TABLE 3c

| Blocking agent | Load (I) | Load (II) |
|---|---|---|
| N-FMOC-β-t-butyl-aspartic-hydroxysuccinimide-ester | 0 | 0.01 |
| N-FMOC-O-t-butyl-L-serine-3,4-dihydro-4-oxo-1,2,3-benztriazole | 0 | 0.02 |
| N-FMOC-L-tenylalanine pentafluorophenyl-ester | 0 | 0.02 |
| N-FMOC-S-trityl-L-cysteine pentafluorophenylester | 0 | 0.01 |
| N-FMOC-L-alanine pentafluorophenylster | 0 | 0.02 |

From these examples it can be seen that active substances with different dimensions can selectively be released from the dendrimer.

With the N-FMOC-L-alanine pentafluorphenylester blocking agent, the active substances I and II are released after a treatment with piperidine followed by a dialysis, in respectively, dimethylformamide and ethanol.

What is claimed is:

1. A composition comprising at least one dendrimer and at least one active substance occluded in said dendrimer, wherein the dendrimer has terminal groups, and wherein a sufficient number of said terminal groups are blocked with blocking agents whereby said active substance is occluded within said dendrimer.

2. A composition according to claim 1, wherein at least a portion of said blocking agents are provided with protective groups.

3. A composition according to claim 1 or 2, wherein the blocking agents are selected from the group consisting of branched or non-branched Michael acceptors, active esters, amino acids, isocyanates, aziridines, acid chlorides, anhydrides, aldehydes, ketones, acrylates, chiral epoxides, and lactones of bislactide.

4. A composition according to claim 1, wherein said blocking agents comprise an amino acid.

5. A composition according to claim 2, wherein the protective group is selected from the group consisting of hydrolyzable esters, ethers, thiol groups, sulphonic acid groups, trityl, silyl, t-butoxy carbonyl, g-fluorenyl methoxy carbonyl, benzyloxy carbonyl, 1,1,4,4-tetramethyl disilyl aza-cyclopentene, and adamantyloxycarbonyl.

6. A composition according to claim 2, wherein the protective group is a t-butoxy carbonyl group.

7. A composition according to claim 2 wherein at least 30% of the terminal groups are provided with a blocking agent with a protective group.

8. A composition according to claim 2 wherein at least 70% of the terminal groups of the dendrimer are provided with a blocking agent with a protective group.

9. A composition according to claim 1, wherein the composition contains more than one active substance.

10. A composition according to claim 1, wherein the active substance is at least one member selected from the group consisting of an agrochemical, pharmaceutical compound, a cosmetic product, an additive for an engineering plastic, a signal absorbing compound, a signal generating compound, a chelating compound, a soap, a colourant, a radioactive labelling compound, a metal, a metal compound, a radionuclide, an electron deficient compound, a nonmetallic electron rich compound, and a precursor thereof.

11. A composition according to claim 1, wherein the dendrimer is a polypropylamine dendrimer.

12. A composition according to claim 11, wherein the dendrimer is a polypropylamine dendrimer and said dendrimer is of at least the fourth generation.

13. A process for the preparation of a dendrimer having at least one active substance occluded therein, which comprises adding an amount of an active substance to be occluded to a reaction mixture containing a dendrimers having terminal groups, and simultaneously or subsequently adding an amount of blocking agent provided with protective groups to block a sufficient number of said terminal groups to effect occlusion of said active substance in said dendrimer.

14. A process for releasing an active substance from a dendrimer having at least one active substance occluded therein wherein said dendrimer has terminal groups, and a sufficient number of said terminal groups are blocked with a blocking agent, which comprises releasing said active substance by splitting off or modifying a blocking-effective amount of the blocking agent.

15. A process for releasing an active substance from a dendrimer having at least one active substance occluded therein wherein said dendrimer has terminal groups, and a sufficient number of said terminal groups are blocked with a blocking agent which is protected with a protective group, which process comprises the step of splitting off a sufficient number of said protecting groups.

16. A process according to claim 15, wherein said process further comprises splitting off or modifying the blocking agent.

* * * * *